United States Patent [19]

Gupta

[11] Patent Number: 4,668,826
[45] Date of Patent: May 26, 1987

[54] PROCESS FOR PRODUCING 2-HYDROXYPHENYL LOWER ALKYL KETONES

[75] Inventor: Balaram B. G. Gupta, North Plainfield, N.J.

[73] Assignee: Celanese Corporation, New York, N.Y.

[21] Appl. No.: 803,194

[22] Filed: Dec. 2, 1985

[51] Int. Cl.$^4$ .............................................. C07C 45/46
[52] U.S. Cl. .................................... 568/319; 560/126
[58] Field of Search ........................ 568/319; 560/129

[56] References Cited

U.S. PATENT DOCUMENTS

| | | | |
|---|---|---|---|
| 3,354,221 | 11/1967 | Landis et al. | 260/592 |
| 3,907,915 | 9/1975 | Chang et al. | 260/668 R |
| 4,283,573 | 8/1981 | Young | 568/794 |
| 4,291,185 | 9/1981 | Koeding | 585/467 |
| 4,371,714 | 2/1983 | Young | 568/628 |
| 4,448,983 | 9/1984 | Young | 560/241.1 |

*Primary Examiner*—James H. Reamer
*Attorney, Agent, or Firm*—Marvin Turken

[57] ABSTRACT

The production of 2-hydroxyphenyl lower alkyl ketones, e.g. 2-hydroxyacetophenone, by reaction of phenol and a lower alkanoic acid, e.g. acetic acid, is carried out by contacting the phenol and acid at an elevated temperature with a ZSM-5 zeolite catalyst having the formula:

$$0.9 \pm 0.2 M_{2/n}O : w_2O_3 : 5-100 yO_2 : zH_2O$$

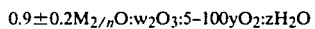

wherein M is a cation, n is the valence of said cation, w is selected from the group consisting of aluminum and gallium, Y is selected from the group consisting of silicon and germanium, and z is from 0 to 40, and in which at least about 80% of the cations are replaced with hydrogen ions. Preferably the catalyst has the formula:

$$0.9 \pm 0.2 M_{2/n}O : Al_2O_3 : 5-100 SiO_2 : zH_2O$$

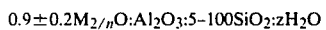

and M is selected from the group consisting of alkali metal cations and tetraalkylammonium cations, the alkyl groups of which preferably contain 2-5 carbon atoms.

12 Claims, No Drawings

PROCESS FOR PRODUCING 2-HYDROXYPHENYL LOWER ALKYL KETONES

This invention relates to a process for producing 2-hydroxyphenyl lower alkyl ketones such as 2-hydroxyacetophenone.

BACKGROUND OF THE INVENTION

Compounds such as 2-hydroxyphenyl lower alkyl ketones, e.g. 2-hydroxyacetophenone (2-HAP) are possible intermediates for a variety of products having different end uses. Thus 2-HAP may be converted into catechol (1,2-dihydroxybenzene) by first reacting the 2-HAP to form the monoacetate ester of catechol using a "Baeyer-Villiger" oxidation as disclosed, for example in application Ser. No. 661,552, filed Oct. 17, 1984 and the references cited therein, and then converting the monoacetate ester to catechol by hydrolysis, e.g. as disclosed in the previously cited application Ser. No. 661,552, or by transesterification as disclosed in Ser. No. 689,533, filed Jan. 7, 1985 and the references cited therein. Alternatively, the 2-HAP can be converted into guaiacol by first methylating it to form 2-methoxyacetophenone, and then obtaining the acetate ester of the monomethyl ether of catechol by a Baeyer-Villiger oxidation and the guaiacol by hydrolysis or transesterification as previously described for catechol. Aspirin may be made from 2-HAP by first acetylating it with acetic anhydride to yield 2-acetoxyacetophenone and oxidizing the latter compound with a transition metal catalyst to form aspirin; these reactions are disclosed in application Ser. No. 633,832 filed July 24, 1984 and the references cited therein.

The reaction of phenol and acetic acid under certain specifically defined conditions to obtain hydroxyacetophenones is disclosed in application Ser. No. 706,016 filed Mar. 26, 1985. Cited in this application are the following published references with teachings of the reaction of phenol and acetic acid to form 4-hydroxyacetophenone (4-HAP), as described:

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, disclose the reaction of phenol and glacial acetic acid in the presence of hydrogen fluoride to produce 4-hydroxyacetophenone (4-HAP) in a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone (4-HAP) in 40% yield.

None of the foregoing disclosures, however, teach any method of reacting phenol with acetic acid to obtain a product comprising a preponderance of 2-HAP.

Various zeolites and zeolite-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of various hydrocarbon conversion processes.

SUMMARY OF THE INVENTION

In accordance with this invention, phenol is reacted with a lower alkanoic acid, e.g. acetic acid, in the presence of an at least partially protonated ZSM-5 zeolite-type catalyst, characterized as an "H-ZSM-5" catalyst, to produce a product comprising a preponderant amount of a 2-hydroxyphenyl lower alkyl ketone, e.g. 2-hydroxyacetophenone (2-HAP). The exact amount of the 2-hydroxyphenyl ketone in the (2-HAP) product may vary depending on conditions with most of the remainder being the corresponding 4-hydroxyphenyl ketone, e.g. 4-hydroxyacetophenone (4-HAP).

The reaction proceeds in accordance with the following equation:

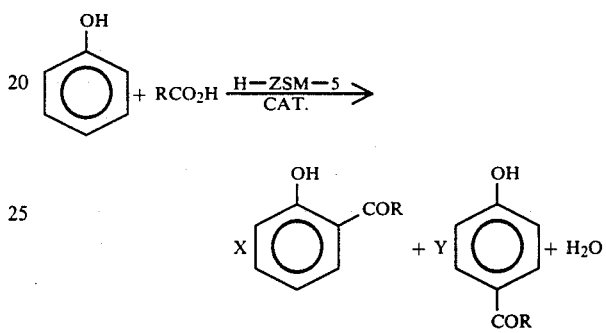

where R is lower alkyl, and X and Y add up to 1 and are the mole fractions, or expressed as percentages, the selectivities of the 2-hydroxyphenyl and 4-hydroxyphenyl ketones respectively based on the total amount of hydroxyphenyl ketones produced in the reaction.

If the lower alkanoic acid is acetic acid, i.e., R is methyl, the reaction proceeds as in the following equation:

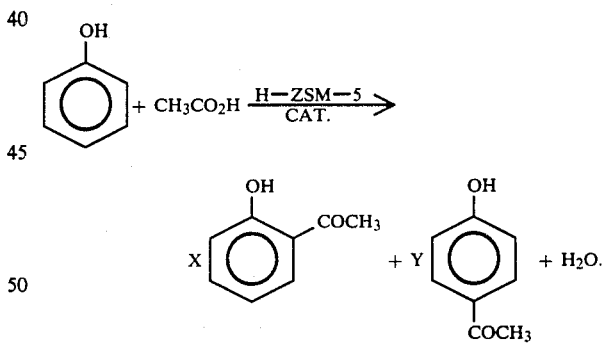

The H-ZSM-5 zeolites utilized as catalysts in the process of this invention are prepared by replacing with hydrogen ions most of the cations of a ZSM-5 zeolite, the composition, characteristics and preparation of which are set out in the previously cited U.S. Pat. No. 3,702,886 of Argauer, the entire disclosure of which is incorporated by reference. These ZSM-5 zeolites have the following formula:

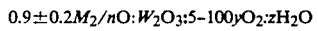

wherein M is a cation, n is the valence of said cation, W is selected from the group consisting of aluminum and gallium, Y is selected from the group consisting of silicon and germanium, and z is from 0 to 40. In a preferred synthesized form, the zeolite has a formula, in terms of mole ratios of oxides, as follows:

$$0.9 \pm 0.2 M_2/nO:Al_2O_3:5\text{-}100SiO_2:zH_2O$$

and M is selected from the group consisting of a mixture of alkali metal cations, especially sodium, and tetraalkyl-ammonium cations, the alkyl groups of which preferably contain 2-5 carbon atoms. In a particularly preferred class of catalysts for purposes of the present invention, the molar ratio of $SiO_2$ to $Al_2O_3$ in the latter formula is within the ratio of about 10 to 60.

The ZSM-5 zeolites in most cases have a distinguishing crystalline structure yielding an X-ray diffraction pattern determined as described in U.S. Pat. No. 2,702,886, with significant lines as indicated in Table I, wherein "s"=strong, "w"=weak and "v.s."=very strong.

TABLE 1

| Interplanar spacing d(A): | Relative intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 ± 0.1 | w. |
| 5.97 | |
| 5.56 ± 0.1 | w. |
| 5.01 ± 0.1 | w. |
| 4.60 ± 0.06 | w. |
| 4.25 ± 0.06 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

The active catalyst in the process of the present invention, characterized as an "H-ZSM-5" zeolite is prepared from a "ZSM-5" zeolite by replacing most, and generally at least about 80% of the cations of the latter zeolite with hydrogen ions using techniques well-known in the art.

As stated, the lower alkanoic acid contemplated to be reacted with phenol under this invention has the formula:

$$R\ CO_2H$$

where R is a lower alkyl. Preferably, R contains 1 to 3 carbon atoms so that the lower alkanoic acid is acetic, propionic, n-butyric or isobutyric acid. The preferred acid is acetic acid which yields 2-HAP as the preferred product.

The reaction may be carried out in the vapor or liquid state under a wide variety of conditions. Reaction temperatures may be employed, for example in the range of about 160° to 350° C., preferably about 200° to 300° C. The pressure is generally uncritical to the reaction and subatmospheric, atmospheric or superatmospheric pressures may be employed. In most cases, however, the pressure of the reaction will be in the range of about 1 to 30 atmospheres absolute.

Although the reaction consumes one mole of phenol per mole of lower alkanoic acid to produce a mole of hydroxyphenyl lower alkyl ketones, the actual molar ratio of phenol to alkanoic acid in the feed stream may be varied between wide limits, e.g. from about 100:1 to 1:100. It is preferred however that such ratio be in the range of about 1:20 to 1:1.

If the phenol and lower alkanoic acid are in the vapor state at the reaction temperature, then they can be fed in undiluted state or diluted with a relatively inert carrier gas, such as nitrogen, argon, helium, carbon dioxide and the like. Likewise, if the reactants are liquid at the reaction temperature, then they also can be used either alone or with a suitable diluent.

It has been found that the presence of water in the reactant feed stream affects the yield of 2-hydroxyphenyl ketone produced. Water is also a principal by-product of the reaction. The molar ratio of water to phenol can range as high as 2 and above. However, an improvement in conversions of phenol and acid can be obtained with concomitant high selectivity to 2-hydroxyphenyl ketones with molar ratios of water to phenol as low as 0.5. Thus, the amount of water utilized can range from about 0.5 mole up to about 2 moles of water per mole of phenol and, preferably, ranges from about 1 to 2 moles of water per mole of phenol feed.

Contact or residence time can also vary widely, depending upon such variables as the lower alkanoic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the zeolite catalyst in conjunction with an inert material such as glass wool to regulate the pressure drop of the reactant stream through the catalyst bed and the contact time of the reactant compounds with the catalyst particles.

The following examples are illustrative embodiments of this invention. Percent conversion is calculated by dividing the moles of total product times 100 by the moles of phenol fed. The selectivity is calculated by dividing the percent conversion to the 2- or 4-hydroxyphenyl ketone by the percent conversion to the total hydroxyacetophenones.

EXAMPLE 1

The catalyst utilized was an H-ZSM-5 zeolite prepared by replacing with hydrogen ions all but 500 ppm based on the weight of the zeolite of the sodium ions in a sodium aluminosilicate ZSM-5 catalyst prepared in accordance with U.S. Pat. No. 3,702,886, in which the ratio of silica to alumina was about 12. About 4.78 g of this catalyst was mixed with 1.28 g of glass wool and charged to an oil heated 14 in. tubular reactor having an inside diameter of about ¼ in. The length of the catalyst bed after charging was about 4.5 in.

A feed liquid was prepared by mixing 23.5 g (0.25 mole) of phenol with 60.0 g (1.0 mole) of acetic acid. About 8 ml/hr of the reaction feed liquid was evaporated and charged to the reactor with an average flow of 187 ml/min. of helium carrier gas at a temperature of 245°–249° C. and pressures before and after the catalyst bed of 244/240 (before/after) psig to 269/257 psig. The vapor effluent was condensed and collected. After four hours the liquid feed was stopped and the passage of helium carrier gas was continued for another 1½ hours to yield 30.50 g of product condensate. Analysis of the condensate indicated the percent conversion to all products including phenyl acetate to be 20.5% and the conversion to hydroxyacetophenones to be 14.5%. Based on the total amount of hydroxyacetophenones produced, the selectivity of 2-HAP was 98.7% and of 4-HAP was 1.3%.

Examples 2 to 5 illustrate the activity of a catalyst bed over a period of time.

EXAMPLE 2

The procedure of Example 1 was followed except that about 4.75 g of the H-ZSM-5 zeolite mixed with 1.35 g of glass wool was charged to the tube reactor, the feed liquid contained 18.8 g (0.2 mole) of phenol and 120.0 g (2.0 mole) of acetic acid, the average flow of the helium carrier gas was 417 ml./mm., the temperature was in the range of 243°–249° C., the pressure before and after the catalyst bed was in the range of 232/222 psig to 244/242 psig, the reactant flow was continued for about 3 hours, and the heating was continued for 2¼ hours after, and the helium flow for about sixteen hours after the reactant feed flow was stopped. Condensate product in an amount of 24.53 g was collected which on analysis indicated percent conversions to all products including phenyl acetate of 37.7% and to hydroxyacetophenones of 13.2%. Based on the total hydroxyacetophenones, the selectivity of 2-HAP was 100%.

EXAMPLE 3

The procedure of Example 2 was followed with the same catalyst bed except that the average helium flow was 321.5 ml./min. for the first hour and under 50 ml./min. for the remainder of the flow period due to plugging, the temperature was in the range of 245°–250° C., the pressure before and after the catalyst bed was in the range of 104/90 psig to 186/168 psig and the heating was continued for 2¾ hours after the reactant feed was stopped. The amount of condensate product collected was 24.53 g which analyzed to 31.3% conversion to all products including phenyl acetate, 6.5% conversion to hydroxyacetophenones, and selectivities to 2-HAP of 96.3% and to 4-HAP of 3.7%, both based on the total conversion to hydroxyacetophenones.

EXAMPLE 4

The procedure of Example 2 was followed with the same catalyst bed except that the average helium flow was 198ml./min., the temperature varied from 295° to 303° C., the pressure before and after the catalyst bed varied from 109/95 psig to 113/95 psig, and the heating was continued for 1½ hours and the helium flow for over 60 hours after the reactant feed stream was stopped. Condensate product was collected in an amount of 24.15 g which on analysis indicated conversions to all products of 36.6% and to hydroxyacetophenones of 7.0% with selectivities of 2-HAP of 90.9% and 4-HAP of 9.1% based on the total hydroxyacetophenones.

EXAMPLE 5

The procedure of Example 2 was followed with the same catalyst bed except that the average helium flow was 253.75 ml./min., the temperature was in the range of 295° to 303° C., the pressure before and after the catalyst bed varied from 115/105 psig to 118/105 psig., the reactant flow was continued for about 4 hours, and 33.54 g of condensate product was collected shortly after the reactant feed stream was stopped. Analysis of the product indicated conversions to all products of 35.0% and to hydroxyacetophenones of 3.1% with selectivities of 2-HAP of 87.0% and 4-HAP of 13.0% based on the total hydroxyacetophenones produced.

EXAMPLES 6 to 8

These examples illustrate the effect of contact time of the reactants over catalyst bed on the product selectivity.

The procedure of Example 2 was followed except for the variation of the reactor pressure and helium carrier gas flow, and the liquid feed was pumped into the vaporizer at the rate of 4 ml/hr the reaction was run for 4 hours. Various other parameters and percent conversions to products are tabulated in Table 2. It is apparent from these results that shorter contact times afford higher conversions to 2-HAP.

TABLE 2

EFFECT OF CONTACT TIME ON THE PRODUCT SELECTIVITY

| Example | Helium Pressure Range (psig) before/after | Average Helium Flow before/after | Contact Time (ml/min) | % Conv. To All (Secs.) Products | % Conv. To HAPS | % Selectivity 2-HAP | 4-HAP | Amt. of Condensate (g) |
|---|---|---|---|---|---|---|---|---|
| 6 | 230/212 | 240/229 | 109.3 | 58.2  31 | 8.7 | 100 | 0 | 14.91 |
| 7 | 205/203 | 235/231 | 103 | 42.1  40 | 10.4 | 100 | 0 | 14.68 |
| 8 | 75/74 | 85/84 | 65.4 | 21.7  48 | 14.4 | 100 | 0 | 17.65 |

EXAMPLES 9 to 13

These Examples illustrate the effect of temperature on the product selectivity.

The procedure of Example 2 was followed except that the average helium flow was between 55–63 ml./min., the pressure before and after the catalyst bed varied from 245/244 psig to 285/280 psig, and the liquid feed was pumped into the vaporizer at the rate of 4 ml/hr. The temperature of the reactor was varied in each of the examples as shown in Table 3 which also shows the amounts of condensate product collected and the percent conversion of phenol to all products including phenyl acetate, and to hydroxyacetophenones (HAPS).

TABLE 3

EFFECT OF TEMPERATURE ON THE ACETYLATION OF PHENOL TO 2-HAP

| Example | Temp. (°C.) | % Conv. To All Products | % Conv. To HAPS | % Selectivity 2-HAP | 4-HAP | Amt. of Condensate (g) |
|---|---|---|---|---|---|---|
| 9 | 200 | 40.0 | 8.0 | 100 | 0 | 16.35 |
| 10 | 220 | 41.2 | 9.4 | 100 | 0 | 15.81 |
| 11 | 250 | 40.0 | 12.8 | 100 | 0 | 16.87 |
| 12 | 270 | 44.6 | 16.2 | 100 | 0 | 16.61 |
| 13 | 300 | 46.0 | 12.7 | 100 | 0 | 17.40 |

EXAMPLE 14

The procedure of Example 1 was followed except that about 4.81 g of the H-ZSM-5 in conjunction with 1.21 g of glass wool was charged to the tube reactor. The feed liquid contained 9.4 g (0.1 mole) of phenol and 74.0 g (1.0 mole) of propionic acid, and the average flow of the helium carrier gas was 175 ml/min. The temperature was in the range of 246°–252° C., and the pressure before and after that catalyst bed was in the range of 90/86 psig to 140/140 psig. After four hours the liquid feed was stopped and the passage of helium carrier gas was continued for another 1½ hours to yield 28.9 g of product condensate. Analysis of the condensate indicated the percent conversion to all products including phenyl propionate to be 40.0% and the conversion to hydroxypropiophenones to be 3.0%. Based on the total amount of hydroxypropiophenones produced, the selectivity to 2-hydroxypropiophenone was 100%.

EXAMPLE 15

The procedure of Example 1 was followed except that about 4.76 g of the H-ZSM-5 in conjunction with 1.25 g of glass wool was charged to the tube reactor, and the feed liquid contained 9.4 g (0.1 mole) of phenol and 88.0 g (1.0 mole) of n-butyric acid. The average flow of the helium carrier gas was 112 ml/min., the temperature was in the range of 245°–254° C., and the pressure before and after the catalyst bed was in the range of 90/89 psig to 95/94 psig. After four hours the liquid feed was stopped and the passage of helium carrier gas was continued for another 1½ hours to yield 33.92 g of product condensate. Analysis of the condensate indicated the percent conversion to all products including phenyl n-butyrate to be 30.0% and the conversion to hydroxy n-butyrophenones to be 2.0%. Based on the total amount of hydroxy n-butyrophenones produced, the selectivity to 2-hydroxy n-butyrophenone was 44%, and to 4-hydroxy-n-butyrophenone was 56%.

Examples 16 and 17 illustrate the effect of water on the product selectivity.

EXAMPLE 16

The procedure of Example 1 was followed except that about 4.86 g of the catalyst together with 1.26 g of glass wool was charged to the tube reactor. The feed liquid contained 9.4 g (0.1 mole) of phenol, 60.0 g (1.0 mole) of acetic acid, and 1.8 g (0.1 mole) of water. The average flow of the helium carrier gas was 328.4 ml/min. The temperature was in the range of 248°–251° C., and the pressure before and after the catalyst bed was in the range of 125/120 psig to 108/102 psig. After four hours the liquid feed was stopped and the passage of helium carrier gas was continued for another 1½ hours to yield 36.48 g of product condensate. Analysis of the condensate indicated the percent conversion to all products including phenyl acetate to be 17.0% and the yield to hydroxyacetophenones to be 4.0%. Based on the total amount of hydroxyacetophenones produced, the selectivity to 2-HAP was 100%.

EXAMPLE 17

The procedure of Example 1 was followed except that about 4.80 g of catalyst together with 1.12 g of glass wool was charged to the tube reactor. The feed liquid contained 9.4 g (0.1 mole) of phenol, 60.0 g (1.0 mole) of acetic acid, and 3.6 g (0.2 mole) of water. The average flow of the helium carrier gas was 295.7 ml/min. The temperature was in the range of 249°–251° C., and the pressure before and after the catalyst bed was in the range of 130/120 psig to 95/94 psig. After four hours the liquid feed was stopped and the passage of helium carrier gas was continued for another 1½ hours to yield 39.31 g of product condensate. Analysis of the condensate indicated the percent conversion of all products including phenyl acetate to be 21.0% and the yield to hydroxyacetophenones to be 13.0%. Based on the total amount of hydroxyacetophenones produced, the selectivity to 2-HAP was 100%.

The following example illustrates the acetylation of phenol by means of the process of this invention utilizing a slurry phase of catalyst in an autoclave.

EXAMPLE 18

A mixture of phenol (9.4 g, 0.1 mole) and acetic acid 60.0 g, 1.0 mole) in a glass liner was slurried with 9.9 g of the catalyst of Example 1 and the liner was inserted into an autoclave. The autoclave was sealed, leak tested, heated to 250° C. (in about 30 mins.) with stirring and maintained at this temperature for 1 hour. At the end of this period, the autoclave was cooled, the volatile gases were vented off, and the liquid slurry was removed. Filtration of this mixture gave 48.4 g of clear liquid. Analysis of this liquid indicated the percent conversion to all products including phenyl acetate to be 31.3% and the yield to hydroxyacetophenones to be 7.0%. Based on the total amount of hydroxyacetophenones produced, the selectivity to 2-HAP was 53.0%, and to 4-HAP was 47.0%.

I claim:

1. A process for the production of a 2-hydroxyphenyl lower alkyl ketone by reaction of phenol with a lower alkanoic acid comprising contacting a feed stream comprising said phenol and acid at an elevated temperature with a ZSM-5 zeolite catalyst having the formula:

$$0.9 \pm 0.2 M_{2/n}O : W_2O_3 : 5\text{--}100 \, YO_2 : zH_2O$$

wherein M is a cation, n is the valence of said cation, W is selecte from the group consisting of aluminum and gallium, Y is selected from the group consisting of silicon and germanium, and z is from 0 to 40, and in which at least about 80% of the cations are replaced with hydrogen ions.

2. The process of claim 1 wherein said ZSM-5 zeolite has an X-ray diffraction pattern with lines as shown in Table 1 of the specification.

3. The process of claim 2 where said catalyst has the formula:

$$0.9 \pm 0.2 M_{2/n}O : Al_2O_3 : 5\text{--}100 \, SiO_2 : zH_2O$$

and M is selected from the group consisting of alkali metal cations and tetraalkylammonium cations, the alkyl groups of which preferably contain 2–5 carbon atoms.

4. The process of claim 3 wherein the ratio of $SiO_2$ to $Al_2O_3$ in said catalyst is in the range of about 10 to 60.

5. The process of claim 3 wherein said lower alkanoic acid is acetic acid and said 2-hydroxyphenyl ketone is 2-hydroxyacetophenone.

6. The process of claim 4 wherein said lower alkanoic acid is acetic acid and said 2-hydroxyphenyl ketone is 2-hydroxyacetophenone.

7. The process of claim 6 wherein said reaction occurs in the vapor phase and said elevated temperature is in the range of about 160° to 350° C.

8. The process of claim 7 wherein said temperature is in the range of about 200° to 300° C.

9. The process of claim 7 wherein said catalyst is in the form of a fixed bed and said feed stream into said bed also contains an inert carrier gas.

10. The process of claim 7 wherein said feed stream also contains about 0.5 to 2 moles of water per mole of phenol.

11. The process of claim 3 wherein the reactants consist of said phenol and alkanoic acid with a molar ratio of phenol to alkonoic acid in the range of about 100:1 to 1:100, the temperature of reaction is in the range of about 160° to 350° C., the pressure of reaction is in the range of about 1 to 30 atmospheres absolute, and the contact time of reactants and catalyst is in the range of about 0.5 to 100 seconds.

12. The process of claim 8 wherein the reactants consist of said phenol and acetic acid with a mole ratio of phenol to acetic acid is in the range of about 1:20 to 1:1, the pressure of reaction is in the range of about 1 to 30 atmospheres absolute, and the contact time of reactants and catalyst is in the range of about 0.5 and 100 seconds.

* * * * *